United States Patent [19]

Chung et al.

[11] 4,328,346

[45] May 4, 1982

[54] SILANE-FUNCTIONALIZED ULTRAVIOLET SCREEN PRECURSORS

[75] Inventors: Rack H. Chung, Clifton Park; William D. Kray, Burnt Hills, both of N.Y.

[73] Assignee: General Electric Company, Waterford, N.Y.

[21] Appl. No.: 174,611

[22] Filed: Aug. 1, 1980

[51] Int. Cl.³ .................................................. C07F 7/18
[52] U.S. Cl. ..................................... 548/110; 556/428; 556/440; 204/159.13
[58] Field of Search .................. 556/428, 440; 548/110

[56] References Cited

U.S. PATENT DOCUMENTS

| Re. 27,281 | 2/1972 | Wilkus et al. | 556/428 X |
|---|---|---|---|
| 2,955,128 | 10/1960 | Bailey | 556/428 |
| 2,968,643 | 1/1961 | Bailey | 556/428 X |
| 3,391,109 | 7/1968 | Wilkus et al. | 556/428 X |
| 3,708,225 | 1/1973 | Misch et al. | 351/160 |
| 3,976,497 | 8/1976 | Clark | 106/287 SE |
| 3,981,897 | 9/1976 | Crivello | 260/440 |
| 3,986,997 | 10/1976 | Clark | 260/29.2 M |
| 4,122,233 | 10/1978 | Proskow | 548/110 X |
| 4,136,102 | 1/1979 | Crivello | 260/440 |
| 4,177,315 | 12/1979 | Ubersax | 428/336 |

*Primary Examiner*—Paul F. Shaver
*Attorney, Agent, or Firm*—Hedman, Casella, Gibson & Costigan

[57] ABSTRACT

Silane-functionalized ultraviolet screening agent precursors comprise compounds of the formula:

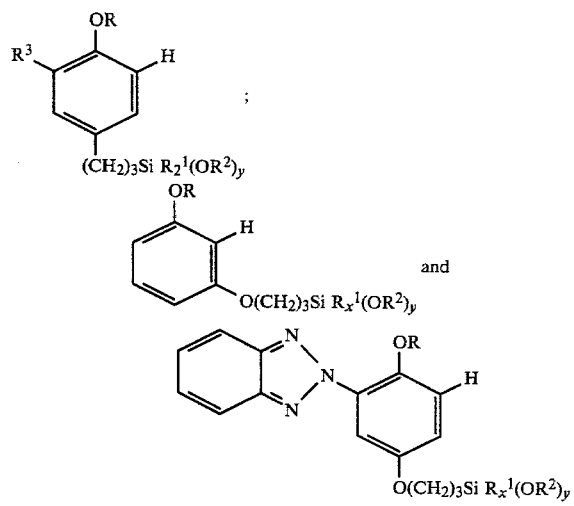

wherein R is

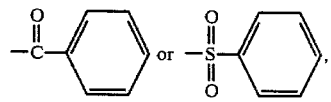

$R^1$ is $C_1$–$C_6$ alkyl, $R^2$ is $C_1$–$C_6$ alkyl or $C_2$–$C_6$ alkanoyl, $R^3$ is hydrogen or $C_1$–$C_6$ alkoxyl, X is 0,1 or 2, y is 1,2, or 3 and $x+y=3$. Under ultraviolet radiation the compounds rearrange to the corresponding α-hydroxybenzophenones which protect substrates, especially transparent plastics, against degradation.

4 Claims, No Drawings

SILANE-FUNCTIONALIZED ULTRAVIOLET SCREEN PRECURSORS

This invention relates to precursors for ultraviolet screening agents. More particularly, it relates to silane-functionalized-phenyl benzoates and -phenyl phenylsulfonates. It is also concerned with ultraviolet curable coating compositions containing the precursors, and to substrates coated with such cured compositions.

BACKGROUND OF THE INVENTION

Many thermoplastics, such as LEXAN ® polycarbonate, require mar-resistant surface coatings to retain transparency under normal operating conditions when used as glazing materials in buildings and in railroad cars, airplanes and the like. A particularly useful family of such coatings are mixtures of silica and hydrolyzable silanes in a hydrolysis medium, such as alcohol and water, see, for example, Misch et al., U.S. Pat. No. 3,708,225; Clark, U.S. Pat. No. 3,986,997 and 3,976,497; and Ubersax, U.S. Pat. No. 4,177,315, as well as in copending application Ser. No. 964,910, filed Nov. 30, 1978. Such coatings are cured thermally, and ultraviolet resistance can be imparted by incorporating a variety of known phenolic ultraviolet (uv) screening agents. These tend to migrate or exhibit plasticizing effects, however, so that silane-functionalization of uv screens, e.g., by forming silylalkyl ether substituents has been developed to insure reaction into the coating composition.

See U.S. Pat. No. 4,278,804 (Ashby et al.); U.S. application Ser. No. 154,621 (Ashby), now allowed, filed May 30, 1980; copending U.S. application Ser. No. 154,625 (Ching), filed May 30, 1980; and U.S. application Ser. No. 154,626 (Ching), now allowed, filed May 30, 1980.

A somewhat more recent development in surface coatings is described in the copending application of Chung, U.S. Ser. No. 129,297, filed Mar. 11, 1980, disclosing ultraviolet light curable silicone hard coating compositions. The various known uv screeners are not effective for such compositions because they retard the curing needed for producing the hardened surface. The foregoing patents and applications are incorporated herein by reference.

It has now been found that functionalized derivatives of precursors of uv screens can be provided, and these will overcome the retardation of uv-curable compositions of the type described in the Chung application. It is further observed that after completion of uv-curing, the precursors will then generate a functionalized uv screen in situ by a photoreaction which is known as a Fries rearrangement. By way of illustration, compound 1 will rearrange to uv-screen 2 as follows:

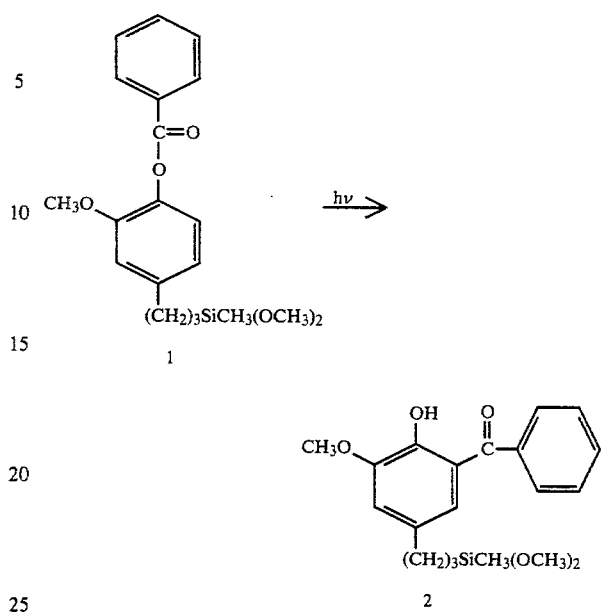

Entirely analogous to this, the precursors contemplated by this invention, as particularly to be described, will undergo a Fries rearrangement to produce hydroxybenzophenone and hydroxyphenyl phenylsulfonyl uv screens which effectively protect, e.g., poly(bisphenol A carbonate) from yellowing under silicone uv-cured hard coats.

Description of the Invention

According to the present invention, there are provided silane-functionalized ultraviolet screening agent precursors selected from compounds of the formulae:

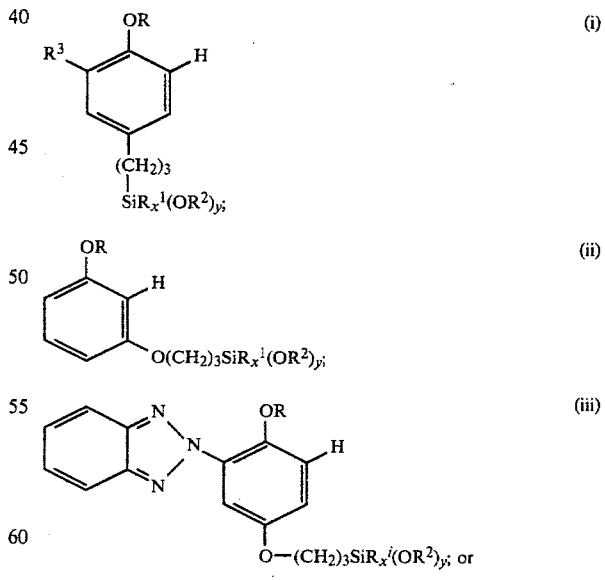

a mixture of any of the foregoing, wherein R is

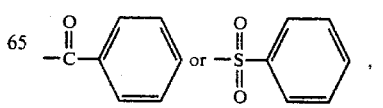

$R^1$ is $C_1$–$C_6$ alkyl, $R^2$ is $R^2$ is $C_1$–$C_6$ alkyl or $C_2$–$C_5$ alkanoyl, $R^3$ is hydrogen or $C_1$–$C_6$ alkoxyl, x is 0,1 or 2, y is 1, 2 or 3, and x+y=3.

In preferred embodiments of compound (i), R is

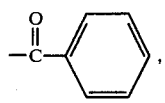

$R^1$ and $R^2$ are $CH_3$, $R^3$ is $OCH_3$, x is 1 and y is z; in compound (ii), R is

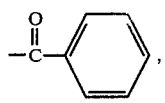

$R^2$ is —$CH_3$ or —$CH_2CH_3$, $R^3$ is H, x is 0 and y is 3; in compound (iii) R is

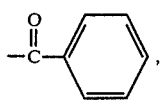

$R^2$ is $CH_3$ or —$CH_2 CH_3$, x is 0 amd y is 3.

The compounds can be used as ultraviolet screening agent precursors in plastics or in coatings, and the like. In preferred embodiments, however, they will be used in coating compositions comprising a mixture of ingredient (A) which is the acid hydrolysis product of an alkoxy-functional silane and ingredient (B) which is the acid hydrolysis product of an acryloxy-functional silane or the acid hydrolysis product of a glycidoxy-functional silane, or mixtures thereof. In the mixture is a catalytic amount of a cationic photoinitiator which is effective for facilitating the ultraviolet cure reaction of the hydrolysis products. Illustrative photoinitiators can be radiation-sensitive halonium, phosphonium or sulfonium salts.

Among the embodiments of the invention, therefore, are radiation curable coating compositions comprising (A) 100 parts by weight of an acid hydrolysis product of an alkoxy-functional silane;

(B) 10 to 1000 parts by weight of
  (i) an acryloxy-functional silane;
  (ii) a glycidoxy-functional silane; or
  (iii) a mixture of (i) and (ii);

(C) a catalytic amount of a photoinitiator; and (D) from 2 to 15 parts by weight of a silane-functionalized ultraviolet agent precursor compound as defined above.

The invention also contemplates substrates coated with such compositions and cured by uv light to provide a hard coating containing the uv screen generated in situ therein.

The compounds of this invention can be made in a number of ways.

Compound (i) is accessible by reacting eugenol, a commercially available material, with benzoyl chloride or benzenesulfonyl chloride, and then adding a hydrosilane across the double bond using a platinum catalyst according to the following pathway:

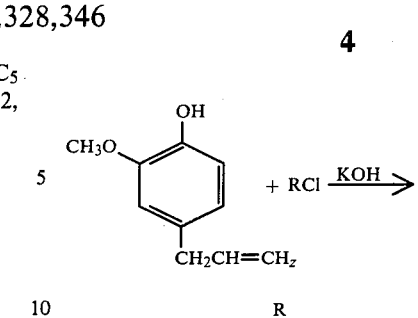

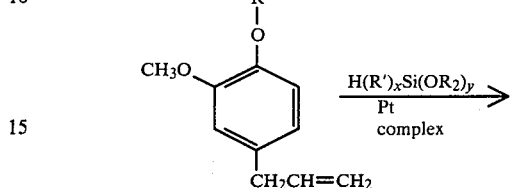

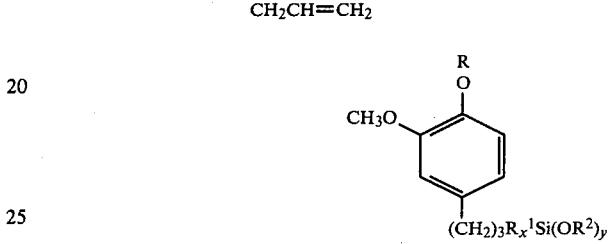

wherein R, $R^1$, $R^2$, x and y are as defined above.

Compound (ii) is accessible by reacting resorcinol with allyl bromide, then with benzoyl chloride or benzenesulfonyl chloride, and finally adding a hydrosilane across the double bond using a platinum catalyst according to the following pathway:

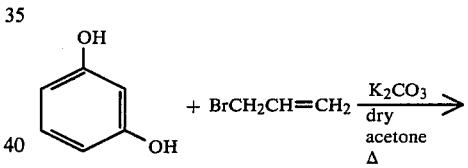

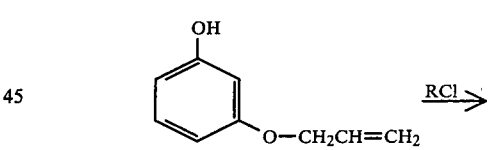

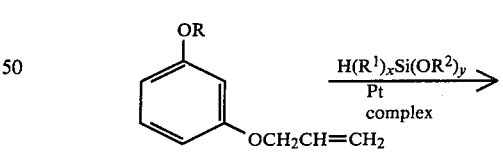

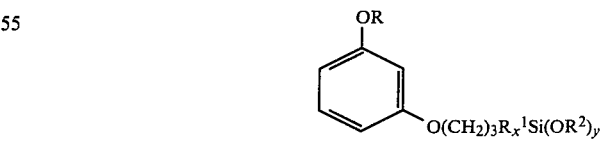

wherein R, $R^1$, $R^2$, x and y are as defined above.

Compound (iii) is accessible by reacting the corresponding substituted phenybenzotriazole with allyl bromide and then with benzoyl chloride or benzenesulfonyl chloride and finally adding a hydrosilane across the double bond using a platinum catalyst according to the following pathway:

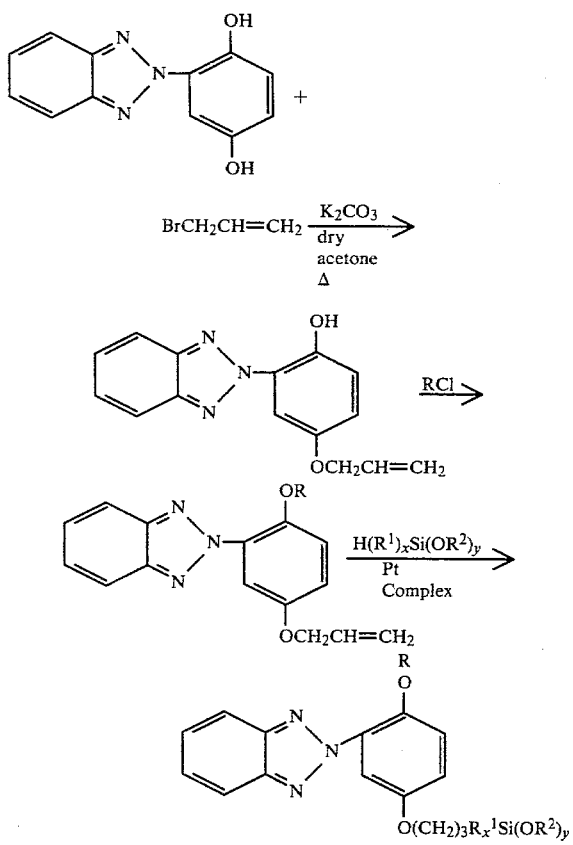

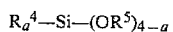

wherein R, R$^1$, R$^2$, x and y are as above-defined.

Examples illustrating the preparation of these embodiments are set forth hereinafter.

With respect to the coating compositions employed in the present invention, one of the major constituents is ingredient (A) which is the hydrolysis product of alkoxy-functional silane. Such a silane will ordinarily have the following general formula:

$$R_a^4\text{—Si—}(OR^5)_{4-a}$$

wherein R$^4$ and R$^5$ are the same or different monovalent hydrocarbon radicals, including halogenated species of such radicals. Preferably, R$^4$ and R$^5$ will be lower alkyl, e.g., C$_1$–C$_6$, radicals such as methyl, ethyl, propyl, etc., but may include other saturated and unsaturated species including vinyl, aryl, etc. The letter a is an integer from 0 to 3 such that there are 4–a alkoxy groups in the silane molecule. Since tetra-alkoxy silanes are particularly effective, a will often equal zero.

The hydrolysis product of such silanes is obtained by contacting the silanes with an excess of water in the presence of a catalytic amount of acid. When less than a stoichiometric amount of water is utilized, a partial-hydrolyzate is obtained. Such partial-hydrolyzates can also be used to obtain the hard coatings of the present invention. Among the particularly useful alkoxy-functional silanes are the following: tetraethoxysilane, ethyltriethoxysilane, diethyldiethoxysilane, triethylethoxysilane, tetramethoxysilane, methyltrimethoxysilane, dimethyldimethoxysilane, and trimethylmethoxysilane.

The second major ingredient is ingredient (B) which is the acid hydrolysis product of an acryloxy-functional silane or the acid hydrolysis product of a glycidoxy-functional silane or mixtures thereof. The acryloxy-functional silane has a general formula given by (II).

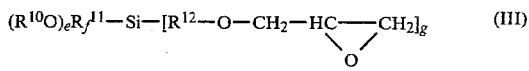

wherein R$^6$ and R$^7$ are the same or different monovalent hydrocarbon radicals as described above for R$^4$ and R$^5$. R$^8$ is a divalent hydrocarbon radical having from 2 to 8 carbon atoms. R$^9$ is a hydrogen or a monovalent hydrocarbon radical. The letter b is an integer from 1 to 3, c is an integer from 0 to 2 and d is an integer equaling 4–b–c. In many of the embodiments of the present invention, b will ordinarily be 3, c will be 0 and d will equal 1. Specific examples of acryloxy-functional silanes include:

3-methacryloxypropyltrimethoxysilane
3-acryloxypropyltrimethoxysilane
2-methacryloxyethyltrimethoxysilane
2-acryloxyethyltrimethoxysilane
3-methacryloxypropyltrimethoxysilane
3-acryloxypropyltriethoxysilane
2-methacryloxyethyltriethoxysilane
2-acryloxyethyltriethoxysilane Such acryloxy-functional silanes are commercially available. For example, 3-methacryloxypropyltrimethoxysilane can be obtained from Union Carbide. The second major constituent (Ingredient B) of the coating composition may also be a glycidoxy-functional silane instead of the acryloxy-functional silane just described, or it may be a combination or mixture of both types of silane. A glycidoxy-functional silane has the general formula given by (III).

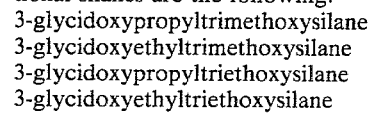

wherein R$^{10}$ and R$^{11}$ are the same or different monovalent hydrocarbon radicals as described above for R$^4$ and R$^5$. R$^{12}$ is a divalent hydrocarbon radical having from 2 to 8 carbon atoms. The letter e is an integer from 1 to 3, f is an integer from 0 to 2 and g is an integer equaling 4–e–f. Specific examples of useful glycidoxy-functional silanes are the following:

3-glycidoxypropyltrimethoxysilane
3-glycidoxyethyltrimethoxysilane
3-glycidoxypropyltriethoxysilane
3-glycidoxyethyltriethoxysilane These glycidoxy-functional silanes are also commercially available. One source, for example, is Petrarch Systems, Inc. The ultraviolet radiation curable coating composition of the present invention will be comprised of 100 parts by weight of the acid hydrolysis product of the alkoxy-functional silane given by formula I which is combined with from approximately 10 to 1000 parts by weight of either the acid hydrolysis product of the acryloxy-functional silane given by formula II or the glycidoxy-functional silane given by formula III, or combinations thereof. To this mixture must be added a catalytic amount of a cationic photoinitiator and from 2 to 15 parts by weight of the ultraviolet agent precursor compound. Effective photoinitiators are radiation sensitive aromatic halonium, sulfonium or phosphonium salts which have been described in the literature.

Cationic photoinitiators have been described by Crivello in numerous U.S. patents and applications, such as the following, for example, which are hereby incorporated by reference: U.S. Pat. Nos. 4,136,102 issued Jan. 23, 1979 and 3,981,897 issued Sept. 21, 1976. Such cationic photoinitiators can have the general formula given by (IV).

  (IV)

In this formula, X is a radical selected from I, P or S. M is a metal or metalloid and Q is a halogen radical selected from Cl, F, Br, or I. $R^{13}$ is hydrogen or a monovalent hydrocarbon radical having from 1 to 12 carbon atoms. The letter h is an integer having the value of 4 to 6 inclusive, an n is an integer having the value of 2 or 3.

The expression $[MQ_h]^-$ applies to any number of ionic species but preferably will be selected from $SbF_6^-$, $AsF_6^-$, $BF_4^-$ and $PF_6^-$.

It is ordinarily preferably to utilize approximately 0.20 parts by weight of the cationic photoinitiator for every 100 parts by weight of the mixture of ingredients A and B as described above. However, depending upon individual desired process parameters such as rate of cure and ultimate abrasion-resistance, the amount of the photoinitiator can range from approximately 0.01 to 5 parts by weight per 100 parts of the mixture of ingredient A and B.

The cationic photoinitiators are particularly effective for initiating a cross-linking reaction between the hydrolyzed alkoxy groups of the compositions given by formulas I, II, and III upon exposure to ultraviolet radiation. Good hard coatings having excellent adhesion can thus be obtained when the coating composition is applied to a substrate and exposed to radiation such as that provided by UV lamps.

The UV-curable coating composition of the present invention is ordinarily coated on at least one surface of some solid substrate. The solid substrate may be comprised of a synthetic organic polymer or a metal or even glass. Also included are synthetic organic polymer substrates which themselves have a metallized surface.

Prior to the composition being coated upon a substrate there may optionally be included a priming step wherein a primer such as a thermosetting acrylic emulsion could first be applied to the substrate. After the coating composition is applied to the substrate or the primed substrate, the coating may be cured thereon and the uv screen generated in situ by exposure to an effective amount of UV-radiation, which may be obtained from, for example, a Hanovia 550 watt lamp or a PPG Processor, Model QC1202.

The coating compositions of the present invention can be applied to a variety of solid substrates by conventional methods, such as flowing, spraying or dipping, to form a continuous surface film. Optimum coating thicknesses are obtained by slow dip coating procedures. Substrates which are especially contemplated herein are transparent and non-transparent plastics and metals. More particularly, these plastics are synthetic organic polymeric substrates such as acrylic polymers like poly(methylmethacrylate), polyesters, such as poly(ethylene terephthalate), poly(butylene terephthalate), etc., polyamides, polyimides, acrylonitrile-styrene copolymers, styrene-acrylonitrile-butadiene copolymers, polyvinyl chloride, butyrates, polyethylene and the like. The coating compositions of this invention are especially useful as coatings for polycarbonates, such as poly(bisphenol-A carbonate) and those polycarbonates known as Lexan ®, sold by General Electric Company, and as coatings for injection molded or extruded acrylics, such as polymethylmethacrylates. Metal substrates on which the present protective coatings are also effective include bright and dull metals like aluminum and bright metallized surfaces like sputtered chromium alloy. Other solid substrates contemplated herein include wood, painted surfaces, leather, glass, ceramics and textiles.

By choice of the proper formulation, application conditions and pretreatment of the substrate including the use of primers, the coatings can be adhered to substantially all solid substrates. A hard coating having all of the aforementioned characteristics and advantages is obtained by the removal of any residual solvent and volatile materials such as methanol or ethanol by-products of the hydrolysis reactions. Note that except for such residual moieties the present invention provides essentially solventless coating compositions.

Coating thicknesses may vary but for improved abrasion-resistance coating thicknesses of 3–10 microns and preferably 5 microns, are utilized.

In order that those skilled in the art may better understand how to practice the present invention, the following examples are given by way of illustration and not by way of limitation.

EXAMPLE 1

(a) 2-Methoxy-4-allylphenyl benzoate

A mixture of 1 mole of 1-allyl-3-hydroxy-4-methoxybenzene (eugenol), 1 mole of potassium hydroxide and one mole of benzoyl chloride in water is stirred at 18°–20° C. for 12 hours under nitrogen. The resulting solid is filtered off and washed with water. Recrystallization from isopropanol yields 2-methoxy-4-allylphenyl benzoate, m.p., 64°–65° C.

(b) 2-Methoxy-4-methyldimethoxysilylpropylphenyl benzoate

To a solution of 1 mole of 2-methoxy-4-allylphenyl benzoate in toluene is added 2 moles of methyldimethoxysilane at 18°–20° C. in the presence of a catalytic amount of a platinum-hydrosilation complex (GE's SPBD-88034). The reaction mixture is evaporated until solvent-free, leaving the product as a pale yellow oil.

The procedure is repeated substituting benzenesulfonyl chloride for benzoyl chloride in step (a) and there is obtained 2-methoxy-4-methyldimethoxysilylpropylphenyl benzenesulfonate.

EXAMPLE 2

(a) 3-Allyloxyphenyl benzoate

In a one-liter, three-necked flask equipped with a thermometer, reflux condenser, dropping funnel, heating mantle and mechanical stirrer are placed 107 g. (0.5 mole) of resoscisol monobenzoate, 500 ml. of dry acetone, and 69 g. (0.5 mole) of potassium carbonate. Seventy-five grams (0.62 mole) of allyl bromide is then added slowly with stirring under nitrogen at about 20° C. After addition of allyl bromide is complete, the mixture is refluxed for 16 hours. The reaction mixture is cooled to about 20° C. and concentrated under reduced pressure. Methylene chloride is added, and washed with dilute sodium bicarbonate solution. The organic layer is dried over anhydrous magnesium sulfate and upon removal of the organic solvent, a light yellow liquid is obtained. The crude material is distilled at 145° C./0.03 mm Hg. to give 98 g. of product.

(b) 3-(3-Trimethoxysilylpropoxy)phenyl benzoate

A mixture of 25.4 g. (0.1 mole) of 3-allyloxyphenyl benzoate, 50 ml. of dry toluene, 20 g. (0.15 mole) of trimethoxysilane and 2 drops of platinum hydrosilation catalyst is heated at 90° C. for 17 hours under nitrogen. After the reaction mixture is cooled to about 20° C., it is concentrated under reduced pressure to produce the uv precursor product. For purification, the product is passed through a short silica column using dichloromethane as an eluent.

EXAMPLE 3

4-(3-Trimethoxysilylpropoxy)-2-(1-N-benzotriazolyl)-phenyl benzoate

Following the same process of Example 2, step (b), the title compound is obtained from the reaction of 37.1 g. (0.1 mole) of 4-allyloxy-2-(1-N-benzotriazolyl)phenyl benzoate, 25 g. (0.2 mole) of trimethoxysilane, 100 ml. of dry toluene, and a catalytic amount of a platinum hydrosilation catalyst.

EXAMPLE 4

A mixture of 52 grams (0.25 mole) of tetraethoxysilane (TES) and 9 grams (0.5 mole) of water is cooled to approximately 0° to 3° C., and 0.4 grams of perchloric acid is added. The reaction mixture is stirred as the ice melts away. After removal of some insoluble particles by filtration, a clear solution of TES-hydrolyzate having a viscosity of 5.6 centistokes is obtained. Next, a second emulsified solution is obtained by mixing 24.8 grams (0.1 mole) of 3-methacryloxypropyltrimethoxysilane (MPTMS) and 2.7 grams (0.15 mole) of water to which 2 drops of perchloric acid are added at room temperature. After stirring overnight at room temperature, a pale, greenish solution of MPTMS-hydrolyzate is obtained having a viscosity of 8.6 centistokes. Into a mixture of 5 grams of TES-hydrolyzate and 4 grams of MPTMS-hydrolyzate is added 60 mg. of a cationic catalyst, diphenyliodoniumhexafluoroarsenate. Then, 1.0 grams of 2-methoxy-4-methyldimethoxysilylpropylphenyl benzoate is added. A clear solution is obtained which is flow coated upon a transparent sheet of Lexan ®, poly(bisphenol A carbonate), and the coated panel is dried at room temperature for 30 minutes. Then it is irradiated under a single Hanovia 550 watt lamp. A hard coating with good adhesion is obtained within 12 to 60 seconds. The panel has excellent resistance to yellowing because uv exposure generates in situ the compound 2-hydroxy-3-methoxy-5-methyldimethoxysilylpropylbenzophenone.

The procedure of Example 4 is repeated, substituting the uv screen precursors of Examples 2 and 3, respectively. Again there are obtained transparent, hard coated poly(bisphenol A carbonate) sheets with excellent resistance to yellowing.

Obviously, many variations will suggest themselves to those skilled in this art in light of the above, detailed description. All such modifications are within the intended scope of the appended claims.

We claim:

1. A silane-functionalized ultraviolet screening agent precursor selected from compounds of the formulae:

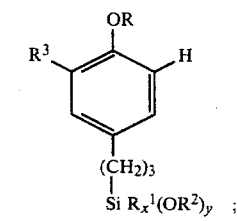

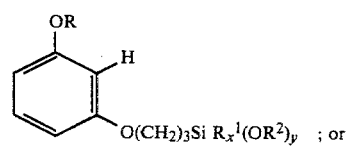

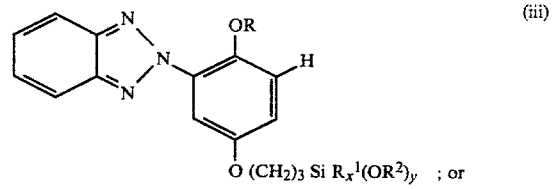

(iv) a mixture of any of the foregoing, wherein R is

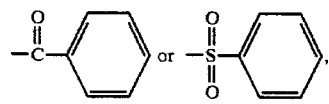

$R^1$ is $C_1$–$C_6$ alkyl, $R^2$ is $C_1$–$C_6$ alkyl or $C_2$–$C_5$ alkanoyl, $R^3$ is hydrogen or $C_1$–$C_6$ alkoxyl, x is 0, 1 or 2, y is 1, 2 or 3, and $x+y=3$.

2. A compound as defined in claim 1 which is of the formula:

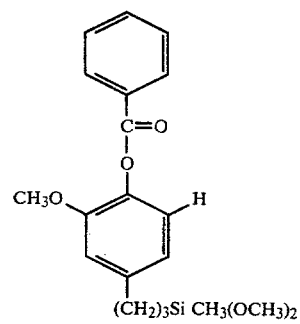

3. A compound as defined in claim 1 which is of the formula:

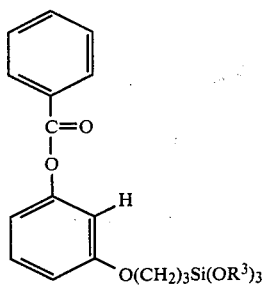
wherein $R^2$ is —$CH_3$, or —$CH_2CH_3$.
4. A compound as defined in claim 1 which is of the formula:
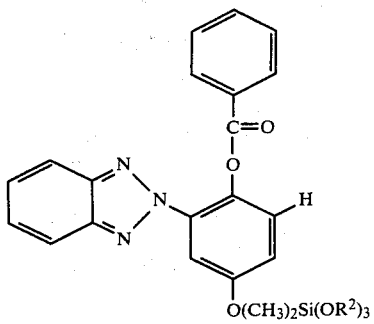
wherein $R^2$ is —$CH_3$ or —$CH_2CH_3$.
* * * * *